United States Patent [19]

Newton et al.

[11] Patent Number: 5,104,663

[45] Date of Patent: * Apr. 14, 1992

[54] TISSUE IRRIGATING SOLUTION

[75] Inventors: Walter A. Newton; Douglas V. Carter, both of Lenoir, N.C.

[73] Assignee: Entravision, Inc., Lenoir, N.C.

[ * ] Notice: The portion of the term of this patent subsequent to Dec. 4, 2007 has been disclaimed.

[21] Appl. No.: 577,306

[22] Filed: Sep. 4, 1990

Related U.S. Application Data

[62] Division of Ser. No. 243,085, Sep. 9, 1988, Pat. No. 4,975,419.

[51] Int. Cl.$^5$ ............... A61K 33/42; A61K 33/14; A61K 37/00; A61K 31/16

[52] U.S. Cl. ............... 424/602; 424/606; 424/678; 424/679; 424/680; 514/2; 514/606; 514/912

[58] Field of Search ............... 424/600, 601, 602, 606, 424/678, 679, 680; 514/912, 606, 6

[56] References Cited

U.S. PATENT DOCUMENTS

| | | | |
|---|---|---|---|
| 4,443,432 | 4/1984 | Garabedian et al. | 424/600 |
| 4,550,022 | 10/1985 | Garabedian et al. | 424/600 |
| 4,975,419 | 12/1990 | Newton et al. | 514/6 |

*Primary Examiner*—Frederick E. Waddell
*Assistant Examiner*—Raymond J. Henley, III
*Attorney, Agent, or Firm*—Rhodes, Coats & Bennett

[57] ABSTRACT

In a tissue irrigating solution of the type containing the combination of glutathione, bicarbonate, and Ringer solution (GBR), the chloride salts (Ringer solution) are packaged and stored in solution and the bicarbonate and glutathione are freeze-dried and packaged and separately stored in powder form until immediately preceeding the operation, at which time the bicarbonate and glutathione are dissolved directly into the solution of chloride salts. The resulting solution is mixed within 24 hours of use.

8 Claims, 2 Drawing Sheets

TISSUE IRRIGATING SOLUTION

This application is a division of application Ser. No. 243,085, filed Sept. 9, 1988, now U.S. Pat. No. 4,975,419.

BACKGROUND OF THE INVENTION

The present invention is directed to tissue irrigating solutions and, more particularly, to an improved technique for formulating and packaging the components of a tissue irrigating solution containing glutathione, bicarbonate, and Ringer solution.

During the surgical procedures, it has been found extremely important to minimize disturbance of the environment of tissue and cells as much as possible. A traumatic change in the environment surrounding internal cells may lead to the destruction of such cells or the destruction of the function of such cells. The destruction of cell function may even lead to destruction of other cells which are dependent upon a proper functioning of the destroyed cells. Therefore, during surgical procedures such as, for example, intraocular surgery, it is very important that the exposed tissue be continuously irrigated with solutions which approximate natural body fluids. Such solutions are called "tissue irrigating solutions". One of the earliest tissue irrigating solutions for ophthalmic procedures was an isotonic saline. However, it was quickly recognized that the isotonic saline was not adequate as an ophthalmic irrigating solution because it resulted in endothelial cell swelling, cell damage, and consequent corneal clouding.

Alternatively, various electrolyte solutions have been proposed as tissue irrigating solutions, particularly in ophthalmic procedures, because such solutions more closely resemble the aqueous humor of the eye. The earliest electrolyte solution was known as Ringer's solution, which was a combination of sodium, calcium and potassium ions along with sodium lactate. Another solution intended for tissue irrigation is known as a balanced salt solution which contains the essential sodium, potassium, calcium, and magnesium salt ions along with an acetate-citrate buffer system. It has been somewhat successful and was used extensively until several years ago. Within the last 10-15 years, there has developed a tissue irrigating solution which is a combination of the Ringer solution along with glutathione and sodium bicarbonate. This is sometimes referred to GBR, and in recent years has become a recognized tissue irrigating solution, especially for ophthalmic procedures. When dextrose, sodium hydrogen phosphate ($Na_2HPO_4$), and sometimes adenosine are added to GBR, there results a fortified or enhanced balanced salt solution (sometimes referred to as "BSS Plus), which has proven to be the most effective for intraocular surgery.

The problem with all GBR solutions and particularly the fortified or enhanced balanced salt solution is that they are not stable. Because they must be mixed essentially at the operative site, it is difficult to control and maintain sterility. There are various reasons why GBR type solutions are not stable. First, bicarbonate and phosphate tend to precipitate in the presence of the magnesium and calcium ions. Therefore, once mixed, the sodium bicarbonate quickly loses its ability to act as a pumping agent for causing the endothelium to perform its fluid transport function of maintaining an outward fluid transport to the stromal layer, which results in damage to the cornea. Stated otherwise, the purpose of the bicarbonate is to act as a pump and, when mixed with the magnesium or calcium ions, it quickly loses its propensity for pumping. A second reason why the GBR solutions are not stable is that bicarbonate decomposes at a pH of less than 8 and be-comes carbon dioxide which again causes the bicarbonate to fail to act as a chemical pump during the surgical procedure. Finally, the glutathione is unstable at a pH greater than 5. Therefore, the glutathione cannot exist in a basic solution and the bicarbonate cannot exist for extended periods in an acid solution.

A solution to this problem has been offered in Garabedian et al. U.S. Pat. Nos. 443,432 and 4,550,022. According to these two patents, initially two solutions are prepared, one a basic solution providing the bicarbonate and sodium phosphate, and the second an acidic solution which provides the calcium and magnesium ions, as well as the dextrose and glutathione. The solutions are packaged and stored separately for extended periods of time and mixed within 24 hours of use. While the resulting irrigating product as described the Garabedian et al technique has achieved some degree of acceptance and success, there are some limitations as a result thereof. The long-term stability and maintenance of acceptable pH values is difficult in accordance with the method and technique described in the Garabedian et al patents. In order to steam sterilize the large solution, it is necessary to place the glutathione in the smaller package, because glutathione cannot stand steam sterilizing. Therefore, since the sodium bicarbonate is in the larger package, the large package must be glass, because it is difficult to maintain the stability of sodium bicarbonate in solution in a polymeric container. This occurs because sodium bicarbonate will not remain stable as a result of the transmission of vapors through the wall of the polypropylene bottle.

SUMMARY OF THE PRESENT INVENTION

In order to overcome the problems described hereinabove and offer an improved formulating and packaging technique, the present invention contemplates a two-part intraocular or tissue irrigating system. A first part includes a stable, sterile pre-packaged acidic solution containing at least the calcium ions and magnesium ions. The second part includes a lyophilized powder containing at least the sodium bicarbonate and glutathione. The sodium hydrogen phosphate is preferably included with the second part (powder). The potassium ions and dextrose may be provided in either the first or second part. When the first and second parts are mixed together, there is formed an extremely satisfactory irrigating solution. Preferably, the powder and solution should be aseptically mixed to maintain the sterility thereof.

More specifically, in the proposed irrigating product, a larger solution (on the order of 500 mls) contains all the chlorides, i.e., sodium, potassium, calcium and magnesium, in a polypropylene bottle that is terminally steam-sterilized according to conventional processes. The second or smaller part is a lyophilized powder which includes sodium bicarbonate, disodium hydrogen phosphate, dextrose and glutathione disulphide. The second part is sterile-filtered before being aseptically filled into either a glass vial or a small polypropylene bottle for lyophil-ization. It has been found preferable to include the sodium hydrogen phosphate with the sodium bicarbonate. Thus the calcium and magnesium ions are placed in the large bottle. Both the bicarbonate and the glutathione are stabilized by the lyophilizing (freeze-drying) process. A special technique has been developed to eliminate any breakdown that could occur before the solution containing bicarbonate and glutathione are frozen. According to the improved technique, the sodium bicarbonate is first frozen, then the glutathione is frozen onto the surface of the sodium bicarbonate, then both frozen components are lyophilized (freeze-dried).

The large solution is preferrably placed in a 500 ml polypropylene bottle and the small solution containing the lyophilized powders are placed in a small 50 ml glass or polypropylene vial. The two components are mixed aseptically through a transfer spike. One end of the spike is inserted through the stopper in the small vial. With the bottle containing the larger amount of solution in the upright position, the small vial is then inverted and the other end of the spike is inserted through the stopper into the large bottle. The large bottle, being polypropylene, is then squeezed which forces a small amount of fluid into the vial which promptly dissolves the lyophilized powder. When the polypropylene bottle is released, the fluid and powder dissolved therein will return to the large bottle. This process is repeated several times to flush all the contents of the vial into the bottle and to thoroughly mix the contents of the two containers.

It is, therefore, an object of the present invention to provide an improved formulating and packaging technique for the manufacture of glutathione/bicarbonate/Ringer solution type products.

Another object of the present invention is to provide an enhanced balanced salt solution of the type described in which the sodium bicarbonate, sodium hydrogen phosphate, and glutathione are packaged together in a powderous form.

Other objects and a fuller understanding of the invention will become apparent upon reading the following detailed description along with the accompanying drawings in which:

FIGS. 1 and 1A illustrate a two-part packaging system in which the components of the irrigating solution of the present invention are prepackaged and stored; and FIG. 2 is a schematic block diagram illustrative of the procedural steps involved in formulating the irrigating solution of present invention.

DETAILED DESCRIPTION OF A PREFERRED EMBODIMENT

Figure 1:
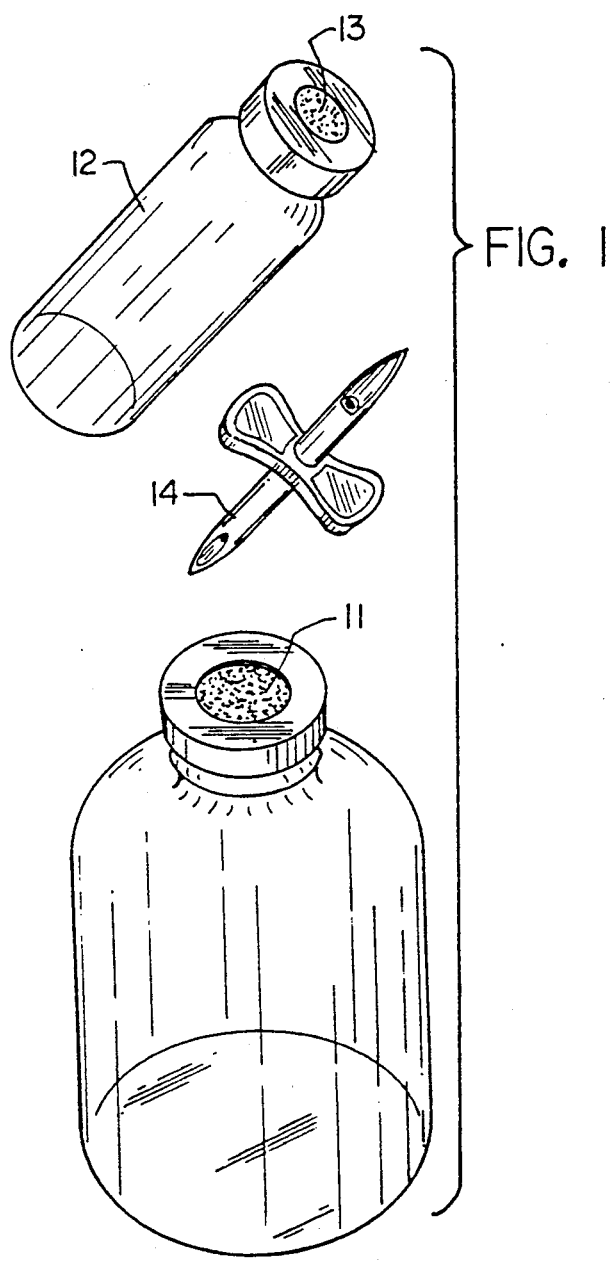
Figure 1A:
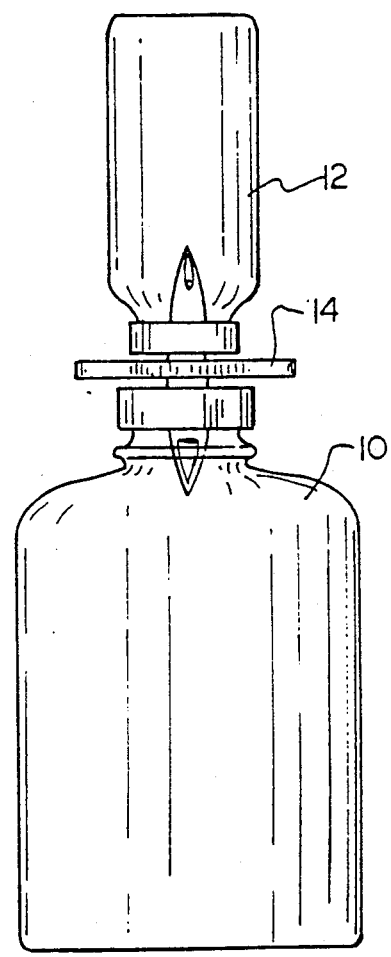
Figure 2:
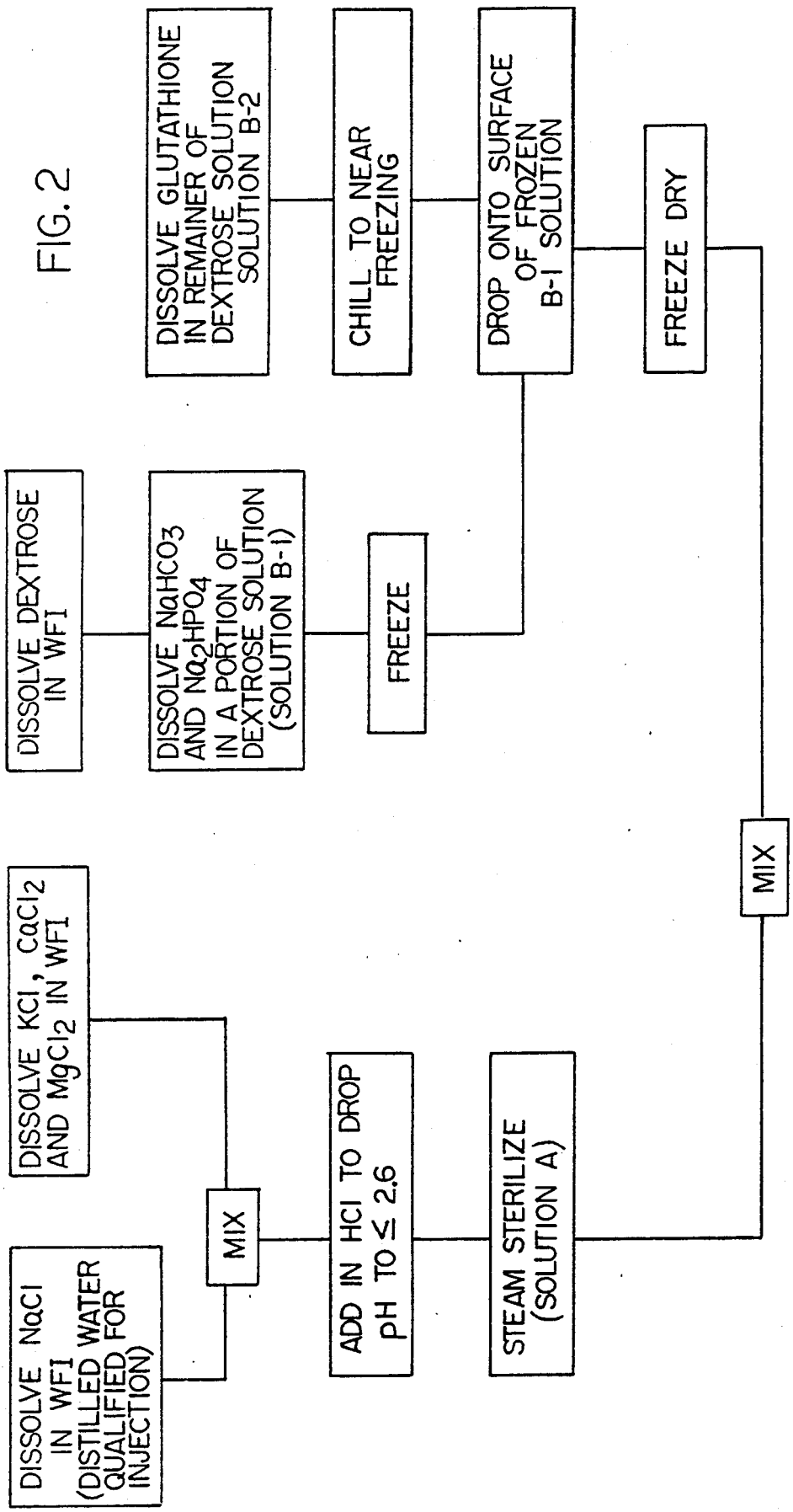

The present invention is directed generally to an improved technique for packaging a tissue irrigating solution of the type which includes glutathione/bicarbonate/Ringer solution, whereby the components are initially packaged in a two-component system. The composition and concentration of the two components of the system are such that they remain stable, even when stored for long periods of time. The two components are separately sterilized, then aseptically mixed so that the ultimate solution is completely sterile and available for use in surgery during the ensuing 24 hours. The mixed solution has been found to be extremely useful for maintaining the appropriate environment and preventing cell damage during surgical procedures, particularly procedures such as intraocular surgery.

The desired irrigating solution, when mixed, preferrably contains the following components in the amount indicated:

| Ingredients for Enhanced Balanced Salt Solution | |
|---|---|
| | mgm/ml |
| Sodium chloride (NaCl) | 7.14 |
| Potassium chloride (KCl) | 0.378 |
| Calcium chloride (CaCl$_2$ 2H$_2$O) | 0.154 |
| Magnesium chloride (MgCl$_2$ 6H$_2$O) | 0.20 |
| Dextrose | 0.916 |
| Sodium carbonate (NaHCO$_3$) | 2.096 |
| Sodium hydrogen phosphate (Na$_2$HPO$_4$) | 0.415 |
| Glutathione disulphide | 0.184 |

As has been described above, the irrigating solution identified hereinabove is supplied in two parts that will be mixed by the end user immediately prior to usage and will have usable life, when mixed, of 6-24 hours. One part is a mixed salt solution shown below in Formula 1 and the second part will be a powder containing the components shown in Formula 2. Formula 2 dissolves readily in Formula 1 and forms a clear solution consisting of the components in the amounts shown above. When packaged and before mixing the Formula 1 and Formula 2 powder contain the following ingredients in the indicated amounts.

| Formula 1 (Solution) | |
|---|---|
| Ingredients | mgm/ml |
| Sodium chloride (NaCl) | 7.14 |
| Potassium chloride (KCl) | 0.378 |
| Calcium chloride (CaCl$_2$ 2H$_2$O) | 0.154 |
| Magnesium chloride (MgCl$_2$ 6H$_2$O) | 0.20 |

| Formula 2 (Powder) | |
|---|---|
| Ingredients | Percentage by Weight |
| Dextrose | 25.3 |
| NaHCO$_3$ | 58.04 |
| Na$_2$HPO$_4$ | 11.49 |
| Glutathione disulphide | 5.10 |

Looking now at the drawing, Formula 1 is placed in the large polypropylene container (500 ml) 10 and Formula 2 is placed in the small container (50 ml) 12. A mixing spike 14 is provided and utilized in the following manner. The mixed salt solution is carried in container 10 and the lyophilized in container 12. One end of the spike 14 is placed through the rubber stopper 13 in vial 12. The vial 12 and spike 14 are then inverted and the other end of the spike is placed through the rubber stopper 11 in the cap of bottle 10. The bottle 10 is preferrably formed of a resilient polypropylene material, so that when it is squeezed, a portion of the fluid is forced up into the small vial, where it mixes with and dissolves the powder therein. When the bottle 10 is released, the fluid then flows back down through spike 14 into the large container. When this process is repeated several times, the powder is fully mixed, dissolved, and transferred into the large container 10. The small vial and spike are then disposed of, and the large container is ready for use in the operative procedure.

In the ensuing examples, there are explained several experiments which were conducted in order to determine the preferred manner for formulating the irrigating solution of the present invention. In preparations for experiments 1-6, the following solutions A and B were prepared.

Solution A

| Ingredients | Amounts |
| --- | --- |
| Distilled water | 10 liters |
| NaCl | 71.4 gms |
| KCl | 3.79 gms |
| $CaCl_2$ | 1.54 gms |
| $MgCl_2$ | 2.00 gms |

Divide Solution A into four equal lots, each lot equaling approximately 2.5 liters, and adjust the pH of each lot with 1N.HCl as follows:

|  | Target | Actual |
| --- | --- | --- |
| Lot 1A | pH 3.0 | pH 2.9 |
| Lot 2A | pH 4.0 | pH 4.1 |
| Lot 3A | pH 5.0 | pH 5.5 |
| Lot 4A | pH 6.0 | pH 6.9 |

Fill nine 250 ml plastic bottles from each pH lot, cap and sterilize. Retain the remaining 25 ml of each lot of Solution A for further observation.

Solution B

| Ingredients | Quantities |
| --- | --- |
| Distilled water | 1 liter |
| $NaHCO_3$ | 42 gms |
| $Na_2HPO_4$ | 8.32 gms |
| Dextrose | 18.4 gms |
| Glutathione | 3.68 gms |

Dissolve the $Na_2HPO_4$ and the dextrose in the one liter of distilled water. Check the pH (8.8). Add glutathione and check the pH again (7.38). Adjust the pH to 7.9-8.0 using 1 N.NaOH solution. Add $NaHCO_3$. Check pH (7.86). Divide the solution into three equal lots and ajdust the pH as follows:

| Lot 1B | pH 7.9-8.0 |
| --- | --- |
| Lot 2B | pH 7.7 |
| Lot 3B | pH 7.4 |

Each of the above lots should be filled into 30 ml glass vials there being 13.25 ml in each of 18 vials of each pH. Freeze dry each vial as soon as possible after mixing.

EXPERIMENT 1

Samples of the freeze-dried Solution B were received and the following tests were performed. First 13.1 mls of water was added to each of two vials of each of the three different types of pH samples and the pH checked immediately and after one hour.

TABLE 1

| Original pH | Sample No. | Reconstituted pH |
| --- | --- | --- |
| 7.6 | (1) | 8.24 |
|  | (2) | 8.23 |
| After 1 hour | (2) | 8.26 |
| 7.73 | (1) | 8.27 |
|  | (2) | 8.28 |
| After 1 hour | (2) | 8.30 |
| 7.86 | (1) | 8.28 |
|  | (2) | 8.28 |

TABLE 1-continued

| Original pH | Sample No. | Reconstituted pH |
| --- | --- | --- |
| After 1 hour | (2) | 8.30 |

Preliminary tests excluded the pH 5 and pH 6 of Solution A as being too high initially. Thereafter, the pH 3 and pH 4 samples of Solution A were used to mix with the three pH levels of freeze-dried Solution B.

TABLE 2

| Mix | Immediate | Three Hour |
| --- | --- | --- |
| 2.9/7.86 | 7.68 | 7.91 |
| 4.1/7.86 | 8.10 | 8.26 |
| 2.9/7.73 | 7.58 | 7.84 |
| 4.1/7.73 | 8.04 | 8.23 |
| 2.9/7.6 | 7.47 | 7.69 |
| 4.1/7.6 | *8.26 | 8.32 |

*This is not a true result as a solution in water from Sample 1 had to be used.

In conclusion as to Experiment 1, it was determined that the pH of Solution B could not be reduced below about 7.9 before freeze-drying. The HCl used to reduce the pH appears to liberate $CO_2$ from the bicarbonate and eventually all free $CO_2$ is lost on freeze-drying. It would, therefore, probably be necessary to have a very low pH (2.0 or less) in Solution A to counteract the buffering effect of the phosphate and the bicarbonate.

EXPERIMENT 2

A fresh batch of Solution A and Solution B were prepared, and the pH of Solution B was adjusted to 7.89 before the $NaHCO_3$ was added. After the addition of $NaHCO_3$, the pH of Solution B was 7.98. The pH of Solution A was adjusted down to 2.5 by using 0.5 N HCl. When Solutions A and B were mixed in the correct proportions (10 ml to 0.5 ml), the pH of the initial mixture was 7.3. After 24 hours, this had risen to pH 8.2 and, thus, did not meet the necessary criteria of pH 7.4.

EXPERIMENT 3

The purpose of Experiments 3 and 4 are to determine by comparison in Experiment 5 what is the best technique for freeze-drying Solution B. In Experiment 3, 18.4 gms of dextrose was dissolved in 1 liter of distilled water. 900 ml of the distilled water/dextrose solution had dissolved in it 8.3 gms of $Na_2HPO_4$ and 42.0 gms of $NaHCO_3$ to form a Solution B-1 having a pH of 8.15.

Using 12 mls of the remaining 100 mls of the dextrose solution, dissolve therein 0.442 gms of glutathione disulphide to form Solution B-2 having a pH of 2.63.

Pipette 11.9 mls of Solution B-1 into each of twelve 30 ml vials, cap and place in a freezer. Cool Solution B-2 to about the freezing point, and when Solution B-1 is frozen and thoroughly chilled, add 1.3 mls of Solution B-2 to each of nine vials of Solution B-1 and return all twelve immediately to the freezer. The second layer of Solution B-2 froze almost immediately on contact with the first layer, which was expected and intended. Retain in the freezer one of the nine vials of the combination solution B-1 and B-2 and one of the three vials of Solution B-1 only. Freeze-dry the remainder for further tests in Experiment 5.

EXPERIMENT 4

Dissolve 18.4 gms of dextrose in 1 liter of distilled water. Into 900 mls of the dextrose solution, dissolve therein 42 gms of NaHCO to form Solution B-1 with a pH of 8.03. Fill 11.9 mls of Solution B-1 into each of twelve vials, stopper and freeze. To the remaining 100 mls of the dextrose solution, add 8.32 gms of $Na_2HPO_4$. When completely dissolved (pH 8–9.5), transfer 12 mls to another container and add 0.442 gms glutathione and dissolve forming a Solution B-2 at pH 7.36. Cool Solution B-2 to about the freezing point and, when Solution B-1 is frozen and thoroughly chilled, add 1.3 mls of Solution B-2 to each of nine vials, and return all twelve immediately to the freezer. In the lab experiment, the second layer again froze almost immediately on contact with the first layer as was intended. Retain in the freezer one of the nine vials of the combination solution B-1 and B-2 and one of three vials of Solution B-1 only. Freeze-dry the remainder for further tests in Experiment 5.

EXPERIMENT 5

The freeze-dried samples from Experiments 3 and 4 were received and the following tests were performed on them. First, the four retained frozen samples were thawed and four equivalent freeze-dried samples were reconstituted with distilled water. The pH of all eight samples was measured with the following results:

TABLE I

|  | Sample | Frozen(A) pH | Freeze-dried(B) pH |
|---|---|---|---|
| Exp. 4, Solution 1 | (1) | 8.24 | 8.32 |
| Exp. 4, Solution 1 & Glutathione | (2) | 7.99 | 8.23 |
| Exp. 5, Solution 1 | (3) | 8.15 | 8.26 |
| Exp. 5, Solution 1 & Glutathione & $Na_2HPO_4$ | (4) | 8.10 | 8.33 |

It was observed that Sample 4-B did not dissolve as rapidly as the other samples, presumably because of "caking" of the phosphate in its anhydrous state.

Next, three samples each of the freeze-dried complete solution (Samples 2 and 4) were reconstituted with exactly 12 mls of distilled water and the final pH checked.

TABLE II

|  | Sample | pH 1 | pH 2 | pH 3 |
|---|---|---|---|---|
| Exp. 4, Solution 1 & Glutathione | (2) | 8.26 | 8.21 | 8.27 |
| Exp. 5, Solution 1 & Glutathione & $Na_2HPO_4$ | (4) | 8.28 | 8.25 | 8.27 |

Mixture 2 went easily into solution whereas Mixture 4 took five minutes to completely dissolve.

In conclusion as to Experiment 5, in both Experiments 3 and 4, there was an increase in the final pH after freeze-drying which indicates some slight loss of $CO_2$ during the process. The fact that the samples without glutathione showed a loss, although somewhat smaller, shows that the bicarbonate is inherently unstable—as is well known—and it will probably be necessary to match the Solution 1 to the freeze-dried component in each lot in a production environment in order to produce a consistent pH in the final mixture. There was no marked difference in the apparant bicarbonate stability between the two experiments. In view of the solution difficulty with Experiment 4 material, it seems reasonable to concentrate on the Experiment 3 approach, i.e., using the $NaHCO_3$ and $Na_2HPO_4$ in Solution B-1 with only the glutathione in Solution B-2. This should help with any possible instability of the glutathione in an alkaline pH.

EXPERIMENT 6

The purpose of this experiment was to now determine whether a Solution A could be formulated with a Solution B-1 from Experiment 3 successfully. Again, it should be kept in mind the purpose of the line of experiments (Exp. 1–6) is to determine whether a solution having a final pH of approximately 7.4 when Solution B is dissolved into it can be attained and whether such pH will remain stable.

A 250 ml bottle of Solution A from Experiment 1 at a pH of 2.9 was used. A vial of freeze-dried Solution B (actually Solution B-1 from Experiment 3) was added and the pH checked at 7.65. A small amount (0.2 mls) of 0.5 N HCl was added resulting in a pH of 7.54. A further small amount (0.2 ml) of 0.5 N HCl was added providing a pH of 7.4. Thereafter, 0.4 mls of 0.5 N HCl was added to a bottle (265 mls) of pH 2.9 Solution A giving a pH of 2.58. When a vial of Solution B (actually Solution B-1 from Experiment 3) was added to this solution, there resulted a final mixture having a pH of 7.41. Four additional bottles of Solution A initially having a pH of 4.1 (Lot 2A) were similarly adjusted to pH values around 2.6 with the following results when mixed with vials of Solution B from either Experiment 3 or Experiment 4.

TABLE I

| Final pH of Solution 1 + vial | pH After 5 min. | 1 hr. | 3 hr. | 24 hr. |
|---|---|---|---|---|
| 2.53 + Solution B (Exp. 3) | 7.2 | 7.22 | 7.32 | 7.4 |
| 2.60 + Solution B (Exp. 3) | 7.36 | 7.33 | 7.36 | 7.42 |
| 2.65 + Solution B (Exp. 4) | 7.45 | 7.4 | 7.4 | 7.51 |
| 2.80 + Solution B (Exp. 4) | 7.65 | 7.59 | 7.67 | 7.73 |

After 48 hours, there were obvious signs of degradation with deposits forming and in the case of the two higher pH values a strong smell of $H_2S$ presumably from glutathione degradation. The two lower pH solutions appeared more stable, with less deposit and no odor.

In conclusion:

1. The bicarbonate and phosphate in the first solution with glutathione only in the smaller second portion is the choice because it affords a better chance of stability for the glutathione with the lower pH and there is no problem of phosphate solubility when it is reconstituted. 2. A final pH of about 7.3 can be achieved by adjusting the chloride solution (Solution A) to about pH 2.6. The higher pH of the final solution appears to be less stable and it appears preferable to hold the final pH to or below 7.4.

EXPERIMENT 7

A pilot batch of the enhanced balanced salt solution in accordance with the above invention was produced to confirm the conclusion set forth in the experiments above. A 15 liter batch of solution A was prepared as follows:

14 liters of WFI (distilled water which has been tested and qualified for injection) were measured into a graduated container and 107.1 gms of NaCl was dissolved therein.

1 liter of WFI had dissolved therein 22.7 gms KCl; 9.24 gms $CaCl_2$; and 12.00 gms of $MgCl_2$.

250 mls of the potassium/calcium/magnesium solution was added to the 14 liters of the NaCl solution and the volume was made up to 15 liters by the addition of further WFI. The initial pH of Solution A was 6.03 and was lowered by the addition of 1 N HCl as follows:

| | |
|---|---|
| 9 mls HCl + | pH 3.02 |
| 4 mls HCl + | pH 2.80 |
| 6 mls HCl + | pH 2.67 |
| 6 mls HCl | pH 2.57 |

At this point, and after thorough mixing, the solution was filled into 250 ml plastic bottles, stoppered, capped and sterilized with Dispersa Balansalt.

Solution B was prepared for freeze-drying in such a way that 10 mls of the B-1 solution was frozen and then 1 ml of the B-2 solution was added on top of of the surface of the B-1 solution. Solution B-1 was prepared by dissolving 22.0 gms of dextrose in 1 liter WFI. Approximately 800 mls of this solution was transferred and had dissolved in it 50 gms of NaHCO3 and 9.9gms of Na2HPO4. Additional amount of the dextrose WFI was added to make up 900 mls and equally distributed throughout 30 ml vials at 10 ml per vial and frozen. This made 90 samples.

90 mls of the remaining dextrose solution was transferred to a flask and in it was dissolved 4.4 gms of glutathione disulphide. This glutathione disulphide solution was chilled to near freezing and 1 ml thereof was added to each of the 90 frozen 10 ml aliquots of the bicarbonate solution. The vials were immediately returned to the freezer and they were subsequently freeze-dried without allowing the material to thaw. Five frozen samples were retained as control samples and 85 were sent for freeze-drying.

After freeze-drying, five vials were taken and the contents mixed with each of the five bottles of Solution A at the pH of the mixtures were measured immediately and after one hour, six hours, and 24 hours, all at room temperature. The following results were obtained:

| Sample | pH Value | | | | |
|---|---|---|---|---|---|
| 2 mm | 1 Hr. | 5 Hrs. | 24 Hrs. | 48 Hrs. | 72 Hrs. |
| 1 7.35 | 7.40 | 7.50 | 7.50 | 7.40 | 7.60 |
| 2 7.40 | 7.40 | 7.45 | 7.50 | 7.40 | 7.60 |
| 3 7.35 | 7.40 | 7.45 | 7.45 | 7.40 | 7.60 |
| 4 7.40 | 7.40 | 7.40 | 7.45 | 7.50 | 7.60 |
| 5 7.40 | 7.40 | 7.50 | 7.50 | 7.55 | 7.65 |

From the preliminary pH measurements, it appears that the process used gives reproducible results and that the mixed product is at least as stable as any other glutathione/bicarbonate/Ringer solution product on the market.

While preferred embodiments of the present invention have been described in detail here and above, it is apparent that various changes and modifications might be made without departing from the scope of the invention which is set forth in the accompanying claims.

What is claimed is:

1. A two-part mix capable of separate packaging and storage for subsequent mixture to form a tissue irrigating solution comprising:
   a) a first part comprising an acidic solution containing calcium ions and magnesium ions;
   b) a second part comprising a lyophilized powder containing sodium bicarbonate and glutathione;
   c) sodium ions, potassium ions, and dextrose, each being added to one of said first and second parts;
   d) said first and second parts exhibiting the characteristics of extended shelf life and when mixed together form a solution for irrigating body tissues during surgery.

2. The two-part mix according to claim 1 wherein said first part comprises said sodium ions and said potassium ions, and said second part comprises said dextrose.

3. The two-part mix according to claim 2 wherein said second part further comprises sodium hydrogen phosphate.

4. The two-part mix according to claim 1 wherein said first part is steam-sterilized.

5. The two-part mix according to claim 1 wherein said first part and said second part are packaged in propylene bottles.

6. The two-part mix according to claim 3 wherein said final solution, where said two parts are mixed, comprises ingredients in the following relation:

| Ingredients for Enhanced Balanced Salt Solution | |
|---|---|
| | mgm/ml |
| Sodium chloride | 7.14 |
| Potassium chloride (KCl) | 0.738 |
| Calcium chloride (CaCl2) 2H2O) | 0.154 |
| Magnesium chloride (MgCl2 6H2O) | 0.20 |
| Dextrose | 0.916 |
| Sodium carbonate (NaHCO3) | 2.096 |
| Sodium hydrogen phosphate (Na2HPO4) | 0.415 |
| Glutathione disulphide | 0.184. |

7. The two-part mix according to claim 3 wherein the first part of said mix comprises ingredients substantially in the following relation:

| Formula 1 (Solution) | |
|---|---|
| Ingredients | mgm/ml |
| Sodium chloride (NaCl) | 7.14 |
| Potassium chloride (KCl) | 0.378 |
| Calcium chloride (CaCl2 2H2O) | 0.154 |
| Magnesium chloride (MgCl2 6H2O) | 0.20 | and wherein said second part comprises ingredients substantially in the following relation:

| Formula 2 (Powder) | |
|---|---|
| Ingredients | Percentage by Weight |
| Dextrose | 25.3 |
| NaHCO3 | 58.04 |
| Na2HPO4 | 11.49 |
| Glutathione disulphide | 5.10 |

8. The two-part mix according to claim 7 wherein the pH of the first part before mixing is no greater than 2.8 and the pH of the final solution, when mixed, is no greater than 7.6.

* * * * *